United States Patent [19]

Hoffmann

[11] Patent Number: 5,442,088

[45] Date of Patent: Aug. 15, 1995

[54] PROCESS FOR THE PREPARATION OF PHOSPHORUS-CONTAINING L-AMINO ACIDS, THEIR DERIVATIVES AND INTERMEDIATES FOR THIS PROCESS

[75] Inventor: Michael Hoffmann, Hofheim, Germany

[73] Assignee: Hoechst Aktiengesellschaft, Frankfurt am Main, Germany

[21] Appl. No.: 271,775

[22] Filed: Jul. 7, 1994

Related U.S. Application Data

[63] Continuation of Ser. No. 862,969, Apr. 3, 1992, abandoned.

[30] Foreign Application Priority Data

Apr. 6, 1991 [JP] Japan .................. 3-4111188

[51] Int. Cl.$^6$ .................. C07C 271/22; C07C 311/19; C07C 227/18; C07F 9/40
[52] U.S. Cl. ...................... 560/12; 558/124; 560/30; 560/38; 560/150; 560/161; 560/172; 562/555; 562/574
[58] Field of Search ............... 558/124; 560/150, 161, 560/172, 12; 562/574

[56] References Cited

U.S. PATENT DOCUMENTS 4,382,812  5/1983  Takematsu et al. .
4,389,488  6/1983  Grabley et al. .
4,499,027  2/1985  Minowa et al. .
(List continued on next page.)

FOREIGN PATENT DOCUMENTS 0127429   5/1984   European Pat. Off. .
0248357  12/1987   European Pat. Off. .
0249188  12/1987   European Pat. Off. .
2856260   7/1979   Germany .
3048612A1 7/1982   Germany .
(List continued on next page.)

OTHER PUBLICATIONS

March, J. *Advanced Organic Chemistry;* Fourth Edition; John Wiley and Sons: New York, 1992; pp. 120–125.
Kosolapoff, G. M. et al. *Organic Phosphorus Compounds;*
(List continued on next page.)

*Primary Examiner*—Mary C. Lee
*Assistant Examiner*—M. Ambrose
*Attorney, Agent, or Firm*—Curtis, Morris & Safford

[57] ABSTRACT

Process for the preparation of phosphorus-containing L-amino acids, their derivatives and intermediates for this process L-amino acids of the formula I and salts thereof,

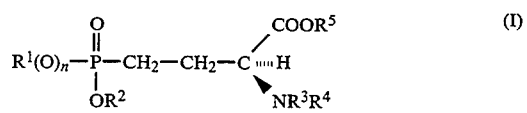

in which $R^1$ to $R^5$ are defined as in claim 1 and n is 0 or 1, are obtained according to the invention by a) reacting an optically active S-homoserine lactone of the formula II,

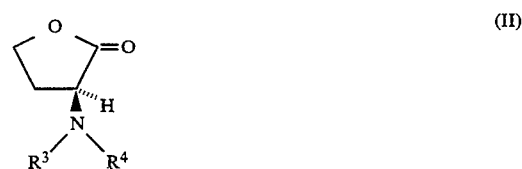

with hydrogen chloride in the presence of an alcohol of the formula $R^5$—OH to give novel compounds of the formula III,

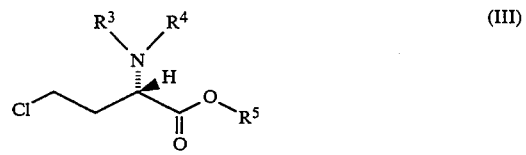

in which $R^3$, $R^4$ and $R^5$ are defined as in formula I, except that $R^5$=H, and b) reacting the resulting compound of formula III with a compound of formula IV, $$R^1(O)_n - R(OR^2)_2 \qquad (IV)$$

and if desired, hydrolyzing the product to give a compound of formula I, in which $R^5$=H.

17 Claims, No Drawings

U.S. PATENT DOCUMENTS

| | | |
|---|---|---|
| 4,552,583 | 11/1985 | Takematsu et al. . |
| 4,777,279 | 10/1988 | Zeiss . |
| 4,922,006 | 5/1990 | Zeiss . |

FOREIGN PATENT DOCUMENTS

| | | |
|---|---|---|
| 3542645A1 | 6/1987 | Germany . |
| 3609818A1 | 9/1987 | Germany . |
| 3817956A1 | 12/1989 | Germany . |
| 220576 | 6/1987 | New Zealand . |

OTHER PUBLICATIONS vol. 7; John Wiley and Sons: New York, 1976; pp. 23–27.

*Chem. Abstr.* 1968, 68(11), 49369p.

*Chem. Abstr.* 1968, 68(11), 50016j.

*Chem. Abstr.* 1968, 69(9), 36449s.

*Chem. Abstr.* 1971, 74(25), 140862k.

*Chem. Abstr.* 1977, 86(25), 190462y.

Barton D. H. R. et al. *Tetrahedron* 1988, 44(17), 5479–5486.

Kosolapoff, G. M. *Organophosphorus Compounds;* John Wiley & Sons: New York, 1950; pp. 121–123.

Liebigs Ann. Chem. 744, 33, 35, 40 (1971).

Bladwin et al., Synthesis and Rearrangement of Homoserine Derivatives, Tetrahedron Letters, vol. 44, No. 2, pp. 637–642, 1988.

Knobler et al., Improved preparation of Intermediates for the Synthesis of a α–Aminobutyric Acid Derivatives having Functional γ–Substituents, J. Chem. Soc. 1958, 1629.

Logusch, Facile Synthesis of D,L–Phosphinothricin from Methyl 4–Bromo–2–Phthalimidobutyrate, Tetrahedron Letters, vol. 27, No. 49, pp. 5935–5938, 1986.

Hanessian et al., A novel and Efficient Synthesis of L–Vinylglycine, Tetrahedron Letters, vol. 25, No. 14, pp. 1425–1428, 1984.

Miyoshi et al., A novel Synthesis of Optically Active Azetidine–2–Carboxylic Acid, Chemistry Letters, pp. 5–6, 1973.

Bajgrowicz et al., Organocuprates Mediated Carbon–Carbon Bond Formation in α–Amino Esters Without Racemisation, Tetrahedron Letters, vol. 25, No. 21, pp. 2231–2234, 1984.

Journal of the American Chemical Society 1990, vol. 112, American Chemical Society G. M. Salituru & C. A. Townsend "Total Syntheses of (−)Nocardicins A–G: A Biogenetic Approach" pp. 760–770.

Bulletin of the Chemical Society of Japan, vol. 40, Nr. 10, 1967, T. Chen "Azetidines II. Some Functional Derivatives of Azetidines" pp. 2398–2401.

PROCESS FOR THE PREPARATION OF PHOSPHORUS-CONTAINING L-AMINO ACIDS, THEIR DERIVATIVES AND INTERMEDIATES FOR THIS PROCESS

This application is a continuation of application Ser. No. 07/862,969, filed Apr. 3, 1992, now abandoned.

DESCRIPTION

Process for the preparation of phosphorus-containing L-amino acids, their derivatives and intermediates for this process The invention relates to processes and intermediates for the preparation of phosphorus-containing L-amino acids of the formula I or their salts,

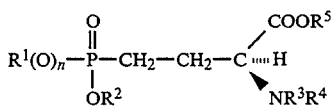

in which $R^1$ and $R^2$ independently of each other are hydrogen, ($C_1$–$C_6$)-alkyl, which is unsubstituted or is mono- or polysubstituted by halogen or aryl, or ($C_3$–$C_{10}$)-cycloalkyl, $R^3$ and $R^4$ independently of each other are hydrogen, ($C_1$–$C_6$)-alkyl, ($C_2$–$C_6$)-alkenyl, ($C_2$–$C_6$)-alkynyl, where the last 3 radicals mentioned can be straight-chain or branched and can have hetero atoms in the chain, ($C_1$–$C_6$)-alkylcarbonyl, aryl-($C_1$–$C_4$)-alkylcarbonyl, ($C_1$–$C_6$)-alkoxycarbonyl, ($C_1$–$C_6$)-alkylsulfonyl, benzyl, benzyloxycarbonyl, aryloxycarbonyl or arylsulfonyl, where the last four radicals mentioned are unsubstituted or substituted in the aryl radical, $R^5$ is hydrogen or ($C_1$–$C_4$)-alkyl, which is straight-chain or branched and is unsubstituted or substituted by halogen, aryl or a heterocycle, or ($C_3$–$C_7$)-cycloalkyl and n is the number 0 or 1.

The compounds of the formula I are disclosed by for example Bull. Chem. Soc. Japan 60, 1761 (1987) and DE-A-2 856 260. Their herbicidal properties are also described there. Compounds to be noted among the compounds of formula I are those in which $R^1(O)_n$=$CH_3$ or $C_2H_5$, $R^2O$=OH and $R^3$, $R^4$ and $R^5$ are each hydrogen, and their salts. The L-form of the herbicide glufosinate (4-[hydroxy(methyl)phosphinoyl]-homoalanine and its salts has particular importance, see the D,L-form in "The Pesticide Manual", 9th Ed. 1990, p. 458; see L-form in DE-A-2856260).

Since according to DE-A-2856260 the herbicidal activity of the L-isomer is twice that of the racemate, the use of the L-isomer offers clear advantages, for example reduced application rate, lower side effects etc.

Phosphorus-containing L-amino acids have been obtained with high optical purity hitherto by laborious, enzymatic racemate resolution processes (DE-A-2939265 and DE-A-3048612).

In addition, there are processes which describe a transamination of the underlying phosphorus-containing α-ketocarboxylic acids (i.e. if in formula I there is a carbonyl group instead of $CHNR^3R^4$) using microorganisms or their transaminases (EP-A-248357, EP-A-249188). A disadvantage of these processes is the poor space-time yield, the technically problematic work-up of the crude solution and the difficult purification of the end products.

Furthermore, there are also processes for enantioselective syntheses of L-amino acid derivatives, which, however, have various disadvantages. Thus, for example the enantioselective alkylation of chiral Schiff bases described in EP-A-127429 gives optical yields of at most only 78%, whereas the asymmetric hydrogenation described in DE-A-3609818 starts from poorly accessible 2,3-dehydroamino acids and catalysts.

In addition, processes are known which start from heterocyclic precursors (DE-A-3542645 and DE-A-3525267). However, these processes have the disadvantage that the respective heterocyclic starting compounds can only be prepared in multi-stage and laborious synthesis steps.

A process is further known which starts with L-glutamic acid (DE-A-3817956). A disadvantage of this process lies in the low yield in the preparation of vinylglycine derivatives, which are the central intermediates in this synthesis (Tetrahedron Lett. 1984, 1425).

In German Patent Application P 4103821.5 a simple process for the preparation of L-homoserine lactones from the cheap and easily accessible L-aspartic acid has already been proposed; it would therefore be an advantage to be able to use L-homoserine lactones as intermediates for the preparation of the phosphorus-containing L-amino acid of formula I.

Processes have now been found for the preparation of the compounds of formula I, which avoid the abovementioned disadvantages and start with easily accessible optically active starting materials.

The invention relates to a process for the preparation of phosphorus-containing L-amino acids of the said formula I or their salts, which comprises a) reacting an optically active S-homoserine lactone of the formula II,

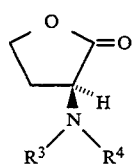

in which $R^3$ and $R^4$ are defined as in formula I, with hydrogen chloride in the presence of an alcohol of the formula $R^5$—OH to give a compound of the formula III

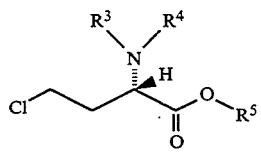

in which $R^3$, $R^4$ and $R^5$ are defined as in formula I, except that $R^5$=H, and b) reacting the resulting compound of formula III with a compound of formula IV,

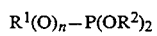

in which $R^1$, $R^2$ and n are defined as in formula I and, if desired, hydrolyzing the product to give the compound of formula I, in which $R^5=H$.

In the formulae mentioned and in the text below, aryl, even in the complex radicals such as arylcarbonyl, is preferably phenyl; substituted aryl or benzyl is preferably phenyl or benzyl, respectively, which is substituted by one or more radicals selected from the group comprising $(C_1-C_4)$-alkyl, $(C_1-C_4)$-alkoxy, halogen, nitro, $(C_1-C_4)$-alkoxycarbonyl, amino, $(C_1-C_4)$-alkylamino and $(C_1-C_4)$-dialkylamino, in particular selected from the group comprising methyl, ethyl, methoxy, ethoxy and halogen. Halogen in the formulae is fluorine, chlorine, bromine or iodine.

Alkyl, alkenyl and alkynyl, which can contain hetero atoms in the chain, are for example such radicals having oxygen atoms or sulfur atoms as hetero atoms, preferably polyoxalkylene radicals having 2 to 5 alkylenoxy units.

Heterocycle is for example an unsubstituted or substituted, aromatic unsaturated or saturated ring having 3 to 7 ring atoms, which can contain 1 to 4 hetero atoms selected from the group comprising O, S and N. Haloalkyl is alkyl which is substituted by one or more halogen atoms.

The invention also relates to processes which correspond to the individual process steps a) and b) of the abovementioned whole process.

The whole process according to the invention thus comprises a lactone ring opening of optically active L-homoserine lactones of formula II, which are easily accessible from L-aspartic acid, using gaseous hydrogen chloride and a subsequent reaction of the chlorides thus obtained of formula III with compounds of the formula IV to give the phosphorus-containing L-amino acids of formula I.

The starting materials of formula II can be easily synthesized from homoserine lactones of formula V

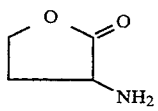 (V)

according to methods known from the literature (Houben-Weyl, volume 15/1, 46–305).

Furthermore, starting materials of formula II, in which one radical of the radicals $R^3$ and $R^4$ is hydrogen, are easily synthesized in a simple manner from aspartic acid derivatives of the formula VI,

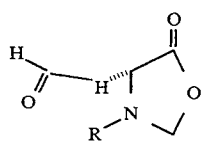 (VI)

in which R has the meaning given for $R^3$ or $R^4$ (see P4103821.5).

Preference is given to processes according to the invention in which $R^1$ and $R^2$ independently of each other are $(C_1-C_4)$-alkyl, $(C_1-C_4)$-haloalkyl, benzyl, 1- or 2-phenylethyl, cyclopentyl or cyclohexyl, in particular methyl or ethyl, $R^3$ and $R^4$ are independently of each other hydrogen $(C_1-C_4)$-alkyl, $(C_1-C_4)$-alkylcarbonyl, phenacetyl, $(C_1-C_4)$-alkoxycarbonyl, $(C_1-C_4)$-alkylsulfonyl, benzyl, benzyloxycarbonyl, phenoxycarbonyl, benzenesulfonyl, where the last 4 radicals mentioned are unsubstituted in the phenyl ring or substituted in the phenyl ring by radicals selected from the group comprising $(C_1-C_3)$-alkyl, $(C_1-C_2)$-alkoxy and halogen, $R^5$ is H, $(C_1-C_4)$-alkyl, $(C_1-C_4)$-haloalkyl, phenyl-$(C_1-C_4)$-alkyl, cyclopentyl or cyclohexyl and n is 0 or 1.

The process according to the invention is carried out, for example, so that in process step a) the lactones of formula II in a suitable aliphatic, cycloaliphatic, araliphatic or heterocyclically substituted aliphatic alcohol, such as for example methanol, ethanol, n-propanol, i-propanol and cyclohexanol, are treated with hydrogen chloride gas at temperatures of 0° C. to reflux temperature, preferably 40° to 70° C.

The preparation of some γ-halo-α-aminobutyric acid derivatives by ring-opening reactions of homoserine lactones with gaseous hydrogen halides is known. However, the known syntheses suffer from various disadvantages.

In the majority of the processes, hydrogen bromide is used for the lactone ring opening (Chemistry Lett., 1973, 5; Tetrahedron Lett., 1986, 27, 5935). This method requires highly stable protecting groups on the amino group. Many protecting groups cannot withstand these acid conditions, which ultimately leads to losses in yield and mixtures of products (Tetrahedron 44 (1988), 637). Certain radicals are cleaved from nitrogen (J. Chem. Soc. 1958, 1629) even when hydrogen chloride is used in ring opening reactions. Since this also involves some of the protecting groups, which should only be removed later under defined conditions in a specific manner, such cleavage reactions are not desirable.

Surprisingly, using the process according to the invention, with the aid of relatively inexpensive hydrogen chloride instead of hydrogen bromide, the desired ring opening can be successfully carried out without racemization and without elimination of protecting groups. The virtually racemization-free ring opening of the compounds of formula II to give the compounds of formula III is all the more surprising as partial racemization occurs with the use of hydrogen iodide (see Tetrahedron Lett. 1984, 2231).

The optically active compounds of the formula III are not only usable as intermediates for the process according to the invention, but are valuable synthons for the preparation of optically active and biologically active compounds. They can thus, for example, be converted into the optically active azetidine-2-carboxylic acid derivatives (JP-49014457). Furthermore, they can be used in the synthesis of nocardicin, a β-lactam antibiotic, (J.Am. Chem. Soc. 112 (1990), 760–770). They can also be used for the preparation of important amino acids such as for example L-canaline (Liebigs Ann. Chem. 1986, 287–291 and literature cited there) or sulfur-containing amino acids (DE-A-2627069). The compounds of formula III obtained according to the invention in process step a) can be selectively hydrolyzed using conventional methods at the ester group to give the corresponding carboxylic acid and can be further reacted with bases to give salts. Moreover, the esters and carboxylic acids of formula III can form acid addition salts. The compounds of the said formula III and their salts are therefore also subject-matter of this invention.

The chlorides of formula III obtained according to the invention are, without intermediate isolation or, preferably after work-up and, optionally, purification in process step b), reacted with phosphorus compounds of formula IV, for example without solvent or in organic solvents, such as aliphatic or aromatic, non-halogenated or halogenated hydrocarbons, such as benzene or toluene, at temperatures of preferably 50° C.–150° C., preferably without solvent at 110° to 140° C. to give the compounds of formula I. In this manner, compounds of formula I are preferably obtained in which $R^1$, $R^2$, $R^3$ and/or $R^4$ and $R^5$ are not hydrogen.

Arbuzov reactions of phosphorus compounds of formula IV with halides differing structurally from those of formula III are known (Chem. Rev. 81 (1981) 415–430 and literature cited there). Furthermore, Arbuzov reactions with racemic ethyl 4-bromo-2-phthalimidobutyrate are known (Tetrahedron Lett., 1986, 5935).

However, it is surprising in the process step b) according to the invention that, for example, the Arbuzov reaction can be carried out with the chlorides of the formula III, although alkyl chlorides are far less reactive than the corresponding bromides (Chem. Rev. 81 (1981) 415–430 and literature cited there), and that no racemization takes place in this Arbuzov reaction in spite of the relatively high reaction temperatures.

Following the reaction of the compounds of the formulae II and III, the resulting compounds of the formula I can be derivatized to give other compounds of the formula I or their salts, for example by hydrolysis of all or part of the hydrolytically cleavable radicals and, possibly, salt formation with bases or acids. An expedient hydrolysis process is for example the acid hydrolysis of compounds of formula I, in which $R^1$, $R^2$ and $R^5$ and at least one radical of the two radicals $R^3$ and $R^4$ are not hydrogen, to give compounds of the formula I in which $R^1$ has the meaning given and $R^2$ to $R^5$ are each hydrogen. For the hydrolysis, the compounds of formula I first obtained are preferably dissolved in aqueous hydrochloric acid (preferably 3N–12N HCl) and heated for several hours at 90° C. to 130° C. The acid, aqueous solution is then extracted with an organic solvent (immiscible or scarcely miscible with water) such as for example toluene, xylene, dichloromethane or methane isobutyl ketone, in order to remove the cleavage products. The aqueous solution is completely evaporated and, if necessary, the crude product is purified by known methods. The hydrochlorides thus obtained of the compounds of the formula I can, if desired, be converted by conventional methods into the free amino acids.

To convert the compounds of formula I into their salts, such compounds having an acidic hydrogen atom are reacted for example with bases, preferably alkaline metal hydroxides or alkaline earth metal hydroxides, alkaline metal carbonates or alkaline earth metal carbonates or alkaline metal hydrogen carbonates or alkaline earth metal hydrogen carbonates or organic amines to give salts usable in crop protection.

Moreover, on account of the constituent amino group, acid addition salts can be prepared, for example with mineral acids such as sulfuric acid, hydrochloric acid, hydrobromic acid, hydroiodic acid, hydrofluoric acid and phosphoric acid or with organic acids, such as formic acid, acetic acid, lactic acid and citric acid.

The process according to the invention delivers the L-isomers of the formula I in high optical yields of over 90% ee, which corresponds to a proportion of more than 95% of the L-isomer. The configuration of the L-forms (Fischer projection) corresponds in the R,S-nomenclature (Cahn, Ingold and Prelog) to the S-configuration.

The process according to the invention thus allows in particular the preparation of optically active γ-chloro-α-aminobutyric acid derivatives of the formula III from easily accessible and optically active homoserine lactones of the formula II and the preparation of optically active phosphorus-containing L-amino acids of the formula I from the easily accessible chlorine compounds of the formula III.

Since the homoserine lactones of the formula II can be prepared from easily accessible L-aspartic acid derivatives, the process according to the invention is an expedient preparation of phosphorus-containing L-amino acids of the formula I using the natural product L-aspartic acid as a chiral pool substance.

EXAMPLE 1

Ethyl (S)-2-(tosylamino)-4-chlorobutyrate

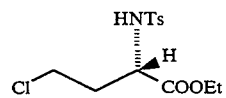

7.5 g (29.4 mmol) of N-p-toluenesulfonyl-L-homoserine lactone (=S-form), prepared according to P 4103821.5, are dissolved in 60 ml of ethanol and heated to 60° C.–70° C. Hydrogen chloride gas is then passed in for 4 h and the reaction solution is subsequently allowed to stand for 12 h at room temperature. The solution is then evaporated to dryness and the crude product is purified by column chromatography on silica gel (mobile phase: heptane/ethyl acetate=3/7); 8 g (89% of theory) of product are obtained as a colorless oil, which begins to crystallize after standing for a relatively long period of time. Characteristic data of the product are:

Specific rotation: $[\alpha]^{25}_D = 10.4$ (c=1, $CH_3OH$);

$^1$H-NMR(100 MHz): δ[ppm]=7.75 and 7.26 (2m, 4H, aromatic-H in —$C_6H_4$—$CH_3$); 5.35 (bd, 1H, NH); 4.10 (m, 1H, CH—N); 4.00 (q, 2H, $COOCH_2$—$CH_3$); 3.65 (t, 2H, —$CH_2Cl$); 2.40 (s, 3H, —$C_6H_4$—$CH_3$); 2.15 (m, 2H, —$CH_2$—$CH_2Cl$); 1.10 (t, 3H, —$COOCH_2CH_3$).

EXAMPLE 2

Ethyl (S)-2-(methoxycarbonylamino)-4-chlorobutyrate

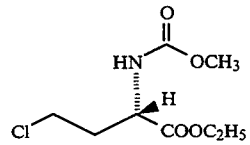

4 g (25 mmol) of N-methoxycarbonyl-L-homoserine lactone (=S-form), prepared according to P 4103821.5, are dissolved in 50 ml of ethanol and heated to 60° C. Hydrogen chloride gas is then passed in for 6 h. The solution is then evaporated to dryness and the crude product is purified by column chromatography on silica gel (mobile phase: heptane/ethyl acetate=1/1); 4.0 g (72% of theory) of product are obtained as a colorless oil with the following characteristic physical data:

Rotation: $[\alpha]^{25}_D = 5.4$ (c=1, $CH_2Cl_2$).

$^1$H-NMR (100 MHz): δ[ppm]=5.40 (bd, 1H, NH); 4.49 (m, 1H, CH—N); 4.22 (q, 2H, —$COOCH_2CH_3$); 3.70 (s, 3H, $COOCH_3$); 3.60 (t, 2H, —$CH_2$—$CH_2Cl$);

2.25 (m, 2H, —CH₂CH₂Cl); 1.30 (t, 3H, —COOCH₂CH₃).

The compounds listed in Table 1 are obtained in an analogous fashion to Examples 1 and 2.

TABLE 1

Compounds of the formula III

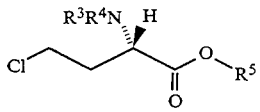

| Ex. No.: | R³ | R⁴ | R⁵ | Phys. data |
|---|---|---|---|---|
| 3 | H | CH₃ | CH₃ | |
| 4 | H | C₂H₅ | CH₃ | |
| 5 | H | n-C₃H₇ | CH₃ | |
| 6 | H | i-C₃H₇ | CH₃ | |
| 7 | H | n-C₄H₉ | CH₃ | |
| 8 | H | CH₂—CH=CH₂ | CH₃ | |
| 9 | H | CH₂C≡CH | CH₃ | |
| 10 | H | —CO—CH₃ | CH₃ | |
| 11 | H | —CO—C₂H₅ | CH₃ | |
| 12 | H | —CO-n-C₃H₇ | CH₃ | |
| 13 | H | —CO—OCH₃ | CH₃ | |
| 14 | H | —CO—OC₂H₅ | CH₃ | |
| 15 | H | —SO₂—CH₃ | CH₃ | |
| 16 | H | —SO₂—C₂H₅ | CH₃ | |
| 17 | H | —CH₂—C₆H₅ | CH₃ | |
| 18 | H | —CO—OCH₂—C₆H₅ | CH₃ | |
| 19 | H | —CO—OC₆H₅ | CH₃ | |
| 20 | H | —CO—O-p-C₆H₄CH₃ | CH₃ | |
| 21 | H | —SO₂—C₆H₅ | CH₃ | |
| 22 | H | —SO₂-p-C₆H₄CH₃ | CH₃ | |
| 23 | H | —CH₂CH₂—OCH₃ | CH₃ | |
| 24 | H | —CH(OCH₃)—CH₃ | CH₃ | |
| 25 | H | n-C₃H₇ | C₂H₅ | |
| 26 | H | i-C₃H₇ | C₂H₅ | |
| 27 | H | n-C₄H₉ | C₂H₅ | |
| 28 | H | CH₂—CH=CH₂ | C₂H₅ | |
| 29 | H | CH₂C≡CH | C₂H₅ | |
| 30 | H | —CO—CH₃ | C₂H₅ | |
| 31 | H | —CO—C₂H₅ | C₂H₅ | |
| 32 | H | —CO—H—C₃H₇ | C₂H₅ | |
| 33 | H | —CO—OCH₃ | C₂H₅ | |
| 34 | H | —CO—OC₂H₅ | C₂H₅ | |
| 35 | H | —SO₂—CH₃ | C₂H₅ | |
| 36 | H | —SO₂—C₂H₅ | C₂H₅ | |
| 37 | H | —CH₂—C₆H₅ | C₂H₅ | |
| 38 | H | —CO—OCH₂C₆H₅ | C₂H₅ | |
| 39 | H | —CO—OC₆H₅ | C₂H₅ | |
| 40 | H | —CO—O-p-C₆H₄CH₃ | C₂H₅ | |
| 41 | H | —SO₂—C₆H₅ | C₂H₅ | |
| 42 | H | —SO₂-p-C₆H₄CH₃ | C₂H₅ | |
| 43 | H | —CH₂CH₂—OCH₃ | C₂H₅ | |
| 44 | H | —CH(OCH₃)—CH₃ | C₂H₅ | |
| 55 | H | CH₃ | C₂H₅ | |
| 56 | H | CH₃ | C₂H₅ | |
| 57 | CH₃ | CH₃ | CH₃ | |
| 58 | C₂H₅ | C₂H₅ | CH₃ | |
| 59 | CH₃ | CH₃ | C₂H₅ | |
| 60 | CH₃ | —CO—CH₃ | CH₃ | |
| 61 | CH₃ | —CO—C₂H₅ | CH₃ | |
| 62 | H | —CO-i-C₃H₇ | CH₃ | |
| 63 | H | —CO—OCH₃ | n-C₃H₇ | |
| 64 | H | —CO—OC₂H₅ | n-C₄H₉ | |
| 65 | H | —SO₂—CH₃ | cyclo-C₆H₁₁ | |
| 66 | H | —SO₂—C₂H₅ | CH₂CH₂Cl | |
| 67 | H | —CH₂—C₆H₅ | CH₃ | |
| 68 | H | —CO—OCH₂—C₆H₅ | —CH₂—⟨tetrahydrofuran⟩ | |
| 69 | H | —CO—OC₆H₅ | C₃H₇ | |
| 70 | H | —CO—O-p-C₆H₄CH₃ | C₃H₇ | |
| 71 | H | —SO₂—C₆H₅ | C₃H₇ | |
| 72 | H | —SO₂-p-C₆H₄CH₃ | C₃H₇ | |
| 73 | H | —CH₂CH₂—OCH₃ | C₃H₇ | |

TABLE 1-continued

Compounds of the formula III

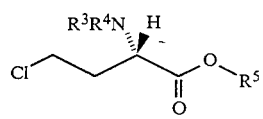

| Ex. No.: | R³ | R⁴ | R⁵ | Phys. data |
|---|---|---|---|---|
| 74 | H | —CH(OCH₃)—CH₃ | C₃H₇ | |

EXAMPLE 75

Ethyl (S)-2-(p-toluenesulfonylamino)-4-[ethoxy(methyl)phosphinyl]butanoate

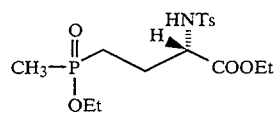

5 g (16.35 mmol) of ethyl (S)-2-(p-toluenesulfonylamino)-4-chlorobutanoate and 9 g (66.13 mmol) of diethyl methanephosphonate are stirred for 15 h at 140° C. Excess diethyl methanephosphonate is then removed under a high vacuum. The crude product thus obtained shows no further organic impurities in ¹H-NMR and is further purified by column chromatography on silica gel (mobile phase: methylene chloride/methanol=95/5); 4.1 g (65%) of product are obtained as a colorless oil having the following physical data:

$[\alpha]^{25}_D = +8.7$ (c=1, MeOH);

¹H-NMR (100 MHz): δ[ppm]=7.73 and 7.29 (2 bd, 4H, —C₆H₄—CH₃); 5.68 (bd, 1H, NH); 4.00 (m, 5H, CH—N, COOCH₂CH₃, —POCH₂); 2.40 (s, 3H, —C₆H₄—CH₃); 1.90 (m, 4H, —CH₂—CH₂—); 1.45 (d, 3H, CH₃—P); 1.30 and 1.13 (2t, 6H, POCH₂CH₃, COOCH₂CH₃).

EXAMPLE 76

Ethyl (S)-2-(methoxycarbonylamino)-4-[ethoxy(methyl)phosphinyl]butanoate

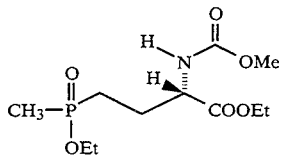

2.6 g (11.6 mmol) of ethyl (S)-2-(methoxycarbonylamino)-4-chlorobutanoate and 6.3 g (46.4 mmol) of diethyl methanephosphonate are stirred for 15 h at 140° C. The excess diethyl methanephosphonate is then removed at 90° C. under a high vacuum. The crude product thus obtained is produced as a colorless oil and shows no further impurities in ¹H-NMR; yield: 2.8 g (82%), ¹H-NMR (100 MHz): δ[ppm]=5.75 (bd, 1H, NH), 4.40 (m, 1H,CH—N); 4.19 and 4.00 (2q, 4H, —COOCH₂CH₃, —POCH₂CH₃); 3.67 (s, 3H, COOCH₃); 1.90 (m, 4H, —CH₂CH₂—); 1.44 (d, 3H, CH₃P); 1.29 and 1.26 (2t, 6H, POCH₂CH₃, COOCH₂CH₃).

EXAMPLE 77

L-Phosphinothricin hydrochloride

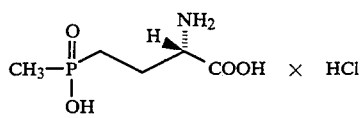

2.8 g (9.5 mmol) of ethyl (S)-2-methoxycarbonylamino-4-ethoxy(methyl)phosphinylbutanoate are boiled in 50 ml of 6N HCl for 12 h under reflux. The aqueous solution is then extracted with dichloromethane, a small amount of activated charcoal is added, the mixture is briefly boiled and, after the activated charcoal is filtered off, is evaporated to dryness. The residue is repeatedly taken up in toluene/acetone and concentrated. 1.5 g (73% of theory) of product are obtained as a colorless solid; ¹H-NMR (100 MHz, D₂O): δ[ppm]=4.16 (t, 1H, CH—N ), 2.10 (m, 4H, —CH₂CH₂—); 1.55 (d, 3H, CH₃—P).

The enantiomeric excess, which was determined with the aid of an HPLC method [J. Chromatogr. 368, 413 (1986)], is 94.2% ee (ee=enantiomeric excess).

I claim:

1. A process for the preparation of a compound of the formula I or salt thereof,

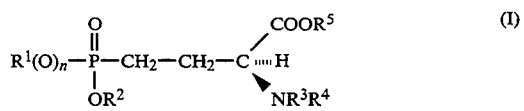

in which

R¹ and R² independently of each other are hydrogen, (C₁-C₆)-alkyl, which is unsubstituted or is mono- or polysubstituted by halogen or aryl, or (C₃-C₁₀)-cycloalkyl, R³ and R⁴ independently of each other are hydrogen, (C₁-C₆)-alkyl, (C₂-C₆)-alkenyl, (C₂-C₆)-alkynyl, where the last three radicals mentioned can be straight-chain or branched and can have hetero atoms in the chain, (C₁-C₆)-alkylcarbonyl, aryl-(C₁-C₄)-alkylcarbonyl, (C₁-C₆)-alkoxycarbonyl, (C₁-C₆)-alkylsulfonyl, benzyl, benzyloxycarbonyl, aryloxycarbonyl or arylsulfonyl, where the last four radicals mentioned are unsubstituted or substituted in the aryl radical, R⁵ is hydrogen or (C₁-C₄)-alkyl, which is straight-chain or branched and is unsubstituted or substituted by halogen, aryl or a heterocycle, or (C₃-C₇)-cycloalkyl and n is the number 0 or 1, which comprises a) reacting an optically active S-homoserine lactone of the formula II,

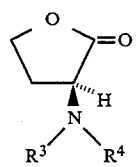

in which

R³ and R⁴ are defined as in formula I, with hydrogen chloride in the presence of an alcohol of the formula R⁵—OH to give a compound of the formula III

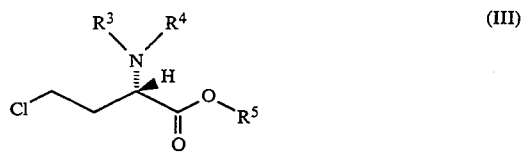

in which

R³, R⁴ and R⁵ are defined as in formula I, except that R⁵=H, and b) reacting the resulting compound of formula III with a compound of formula IV,

in which

R¹, R² and n are defined as in formula I and, if desired, hydrolyzing the product to give the compound of formula I, in which R⁵=H.

2. The process as claimed in claim 1, wherein R¹ and R² independently of each other are (C₁-C₄)-alkyl, (C₁-C₄)-haloalkyl, benzyl, 1- or 2-phenylethyl, cyclopentyl or cyclohexyl, R³ and R⁴ are independently of each other hydrogen (C₁C₄)-alkyl, (C₁-C₄)-alkylcarbonyl, phenacetyl, (C₁-C₄)-alkoxycarbonyl, (C₁-C₄)-alkylsulfonyl, benzyl, benzyloxycarbonyl, phenoxycarbonyl, benzenesulfonyl, where the last 4 radicals mentioned are unsubstituted in the phenyl ring or substituted in the phenyl ring by radicals selected from the group consisting of (C₁-C₃)-alkyl, (C₁-C₂)-alkoxy and halogen, R⁵ is H, (C₁-C₄)-alkyl, (C₁-C₄)-haloalkyl, phenyl-(C₁-C₄)-alkyl, cyclopentyl or cyclohexyl and n is 0 or 1.

3. The process as claimed in claim 1, wherein in process step a), the reaction is carried out at 0° C. up to the reflux temperature.

4. The process as claimed in claim 3, wherein the temperature is 40° to 70° C.

5. The process as claimed in claim 1, wherein the alcohol R⁵—OH in process step a) is methanol, ethanol, n-propanol, i-propanol or cyclohexanol.

6. The process as claimed in claim 1, wherein the reaction in process step b) is carried out in the absence of solvent at 50° to 150° C.

7. A process for the preparation of a compound of formula III

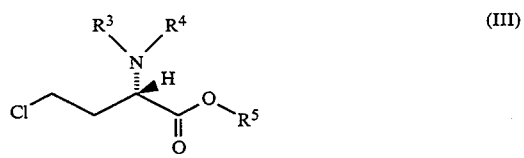

which comprises reacting a compound of formula II

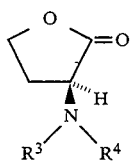 (II)

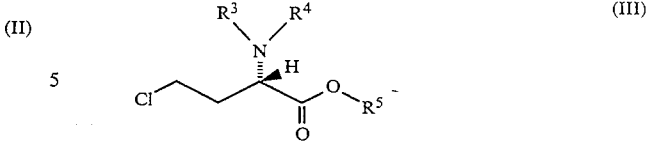 (III)

with hydrogen chloride in the presence of an alcohol of the formula $R^5$—OH, and, if desired, hydrolyzing the product to give the compound of formula III in which $R^5=H$ wherein:

$R^3$ and $R^4$ independently of each other are hydrogen, $(C_1-C_6)$-alkyl, $(C_2-C_6)$-alkenyl, $(C_2-C_6)$-alkynyl, where the last three radicals mentioned can be straight-chain or branched and can have hetero atoms in the chain, $(C_1-C_6)$-alkylcarbonyl, aryl-$(C_1-C_4)$-alkylcarbonyl, $(C_1-C_6)$-alkoxycarbonyl, $(C_1-C_6)$-alkylsulfonyl, benzyl, benzyloxycarbonyl, aryloxycarbonyl or arylsulfonyl, where the last four radicals mentioned are unsubstituted or substituted in the aryl radical, and $R^5$ is hydrogen or $(C_1-C_4)$-alkyl, which is straight-chain or branched and is unsubstituted or substituted by halogen, aryl or a heterocycle, or $(C_3-C_7)$-cycloalkyl.

8. The process as claimed in claim 7, wherein the reaction is carried out at 0° C. up to reflux temperature.

9. The process as claimed in claim 8, wherein the temperature is 40° to 70° C.

10. The process as claimed in claim 7, wherein the alcohol $R^5$—OH is methanol, ethanol, n-propanol, i-propanol or cyclohexanol.

11. A process for the preparation of a compound of the formula I or salt thereof, as defined in claim 1, which comprises reacting a compound of the formula III, in which
$R^3$, $R^4$ and $R^5$ are defined as in formula I, except that $R^5=H$, with a compound of the formula IV, $$R^1(O)_n-P(OR^2)_2 \qquad (IV)$$

in which $R^1$ and $R^2$ are defined as in formula I, and, if desired, hydrolyzing the product to give the compound of the formula I, in which $R^5=H$.

12. The process as claimed in claim 11, wherein the reaction is carried out at 50° to 150° C.

13. The process as claimed in claim 12, wherein the reaction is carried out in the absence of solvent.

14. The process as claimed in claim 13, wherein the reaction is carried out at 110° to 140° C.

15. The process as claimed in claim 11, wherein the compound obtained of the formula I is hydrolyzed with 3N to 12N aqueous hydrochloric acid at 90° to 130° C. to give the compound of the formula I, in which $R^5=H$.

16. A compound of the formula III or a salt thereof

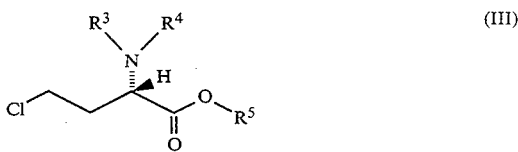 (III)

wherein: $R^3$ is H, $R^4$ is p-tosyl, and $R^5$ is ethyl.

17. A compound of the formula III or a salt thereof

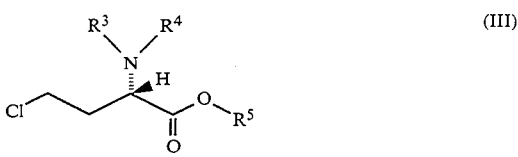 (III)

wherein: $R^3$ is H, $R^4$ is methoxycarbonyl, and $R^5$ is ethyl.

* * * * *